United States Patent [19]

Josef

[11] Patent Number: 5,506,146
[45] Date of Patent: Apr. 9, 1996

[54] MEASUREMENT OF THE ACTIVATED PARTIAL THROMBOPLASTIN TIME (APTT) IN A ONE-STEP REACTION

[75] Inventor: Dieter Josef, Cressier, Switzerland

[73] Assignee: Stiftung Für Diagnostische Forschung, Praz-Rond, Germany

[21] Appl. No.: 266,704

[22] Filed: Jun. 28, 1994

[30] Foreign Application Priority Data

Jun. 30, 1993 [EP] European Pat. Off. ............. 93110471

[51] Int. Cl.$^6$ .................................................. G01N 21/17
[52] U.S. Cl. .............................. 436/69; 436/34; 435/13; 514/2; 530/383
[58] Field of Search ................ 436/69, 34; 435/13, 435/810; 514/2; 530/383

[56] References Cited

U.S. PATENT DOCUMENTS

| | | | |
|---|---|---|---|
| 4,470,968 | 9/1984 | Mitra et al. | 424/101 |
| 4,480,029 | 10/1984 | Dolana | 435/5 |
| 4,495,278 | 1/1985 | Thomas | 435/5 |
| 5,039,617 | 8/1991 | McDonald et al. | 436/69 |
| 5,055,412 | 10/1991 | Proksch | 436/69 |
| 5,059,525 | 10/1991 | Bartl et al. | 435/13 |
| 5,086,002 | 2/1992 | Hillyard et al. | 436/540 |
| 5,091,304 | 2/1992 | La Duca et al. | 435/13 |
| 5,169,786 | 12/1992 | Carroll et al. | 436/69 |
| 5,288,612 | 2/1994 | Griffin et al. | 435/23 |

FOREIGN PATENT DOCUMENTS

| | | |
|---|---|---|
| 0123883 | 11/1984 | European Pat. Off. |
| 0394070 | 10/1990 | European Pat. Off. |
| 0406971 | 1/1991 | European Pat. Off. |
| 0535799 | 4/1993 | European Pat. Off. |

OTHER PUBLICATIONS

Oberhardt et al., *Clin. Chem.*, "Dry Reagent Thechnology for Rapid, Convenient Measurements of Blood Coagulation and Fibrinolysis", 37/4, 520–526 (1991).
Ponjee et al., *Clin. Chem.*, "One–Step Chromogenic Equivalent of Activated Partial Thromboplastin Time Evaluated for Clinical Application", 37/7, 1235–1244 (1991).
Harenberg et al., *Haemostasis*, "Comparative Study on a New One–Stage Clotting Assay for Heparin and its Low Molecular Weight Derivatives", 1989, 1:13–20.
International Publication No. WO 90/11368, published Oct. 4, 1990.

*Primary Examiner*—Timothy M. McMahon
*Assistant Examiner*—N. Bhat
*Attorney, Agent, or Firm*—Nikaido, Marmelstein, Murray & Oram

[57] ABSTRACT

A method for the determination of the activated partial thromboplastin time (APTT) in a one-step reaction, in which the determination of APTT is initiated by contacting a reagent that contains the substances necessary for the APTT determination in a premixed form, with the sample to be tested. A reagent which contains the substances necessary for the APTT determination is also disclosed.

21 Claims, 4 Drawing Sheets

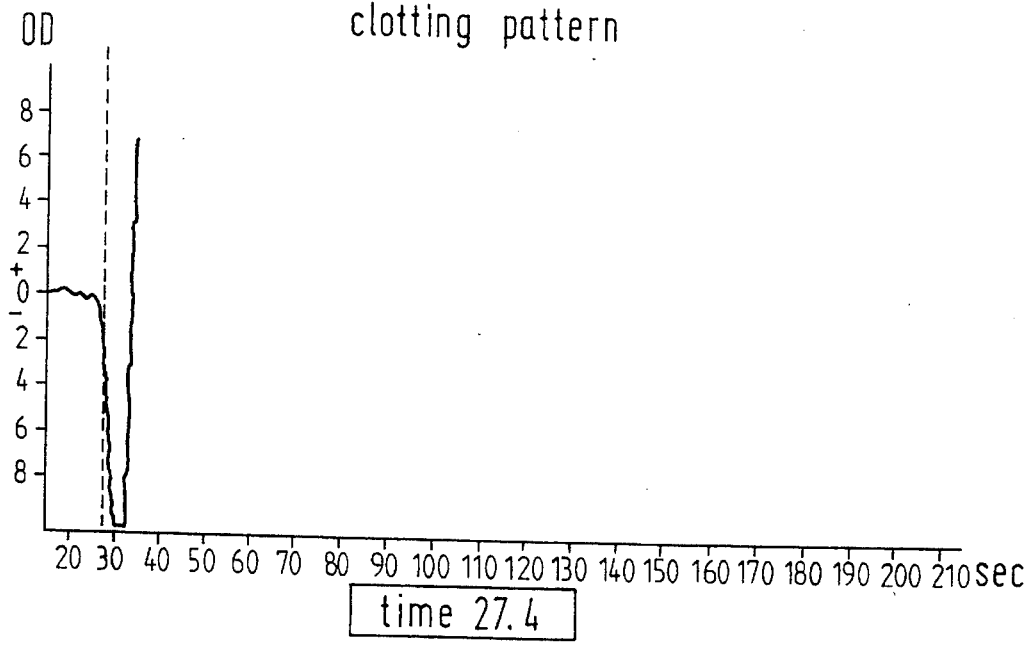
Fig.1a clotting pattern
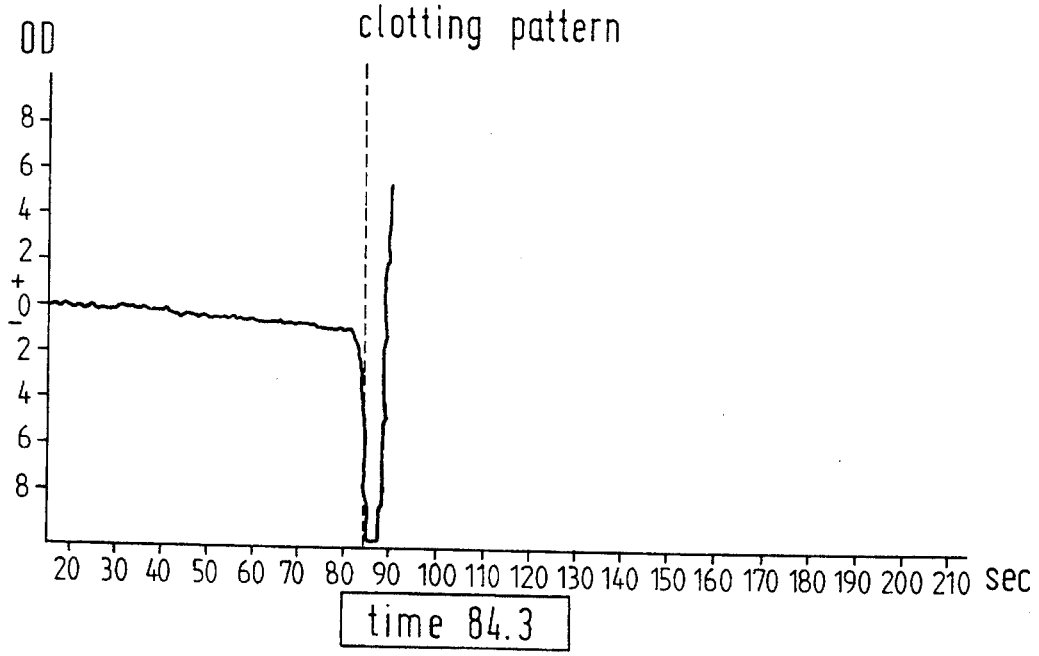
Fig.1b clotting pattern

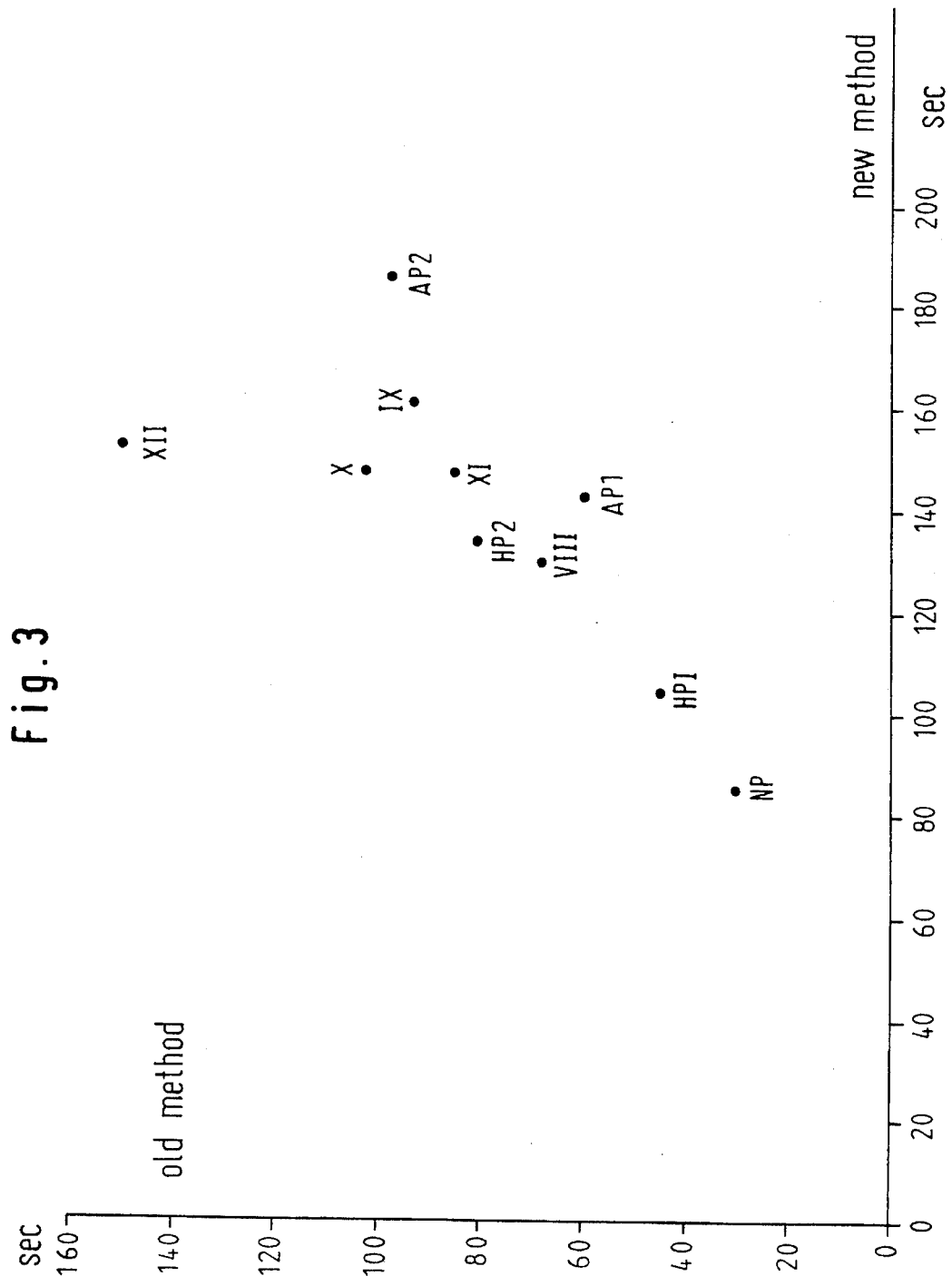

MEASUREMENT OF THE ACTIVATED PARTIAL THROMBOPLASTIN TIME (APTT) IN A ONE-STEP REACTION

DESCRIPTION

The present invention concerns a method and a reagent for the determination of the activated partial thromboplastin time (APTT) in a one-step reaction. The method and reagent according to the invention are particularly suitable for determinations in which APTT is carried out together with determinations of other parameters of the blood coagulation system.

The determination of the activated partial thromboplastin time (APTT) is one of the measurements that are carried out most frequently in coagulation analytics. It mainly serves to detect factor deficiencies in the plasma of patients such as a lack of decrease in factor VIII and to monitor heparin therapy.

The analysis is usually carried out as follows: a sample of the patient's plasma is admixed with an activator. Factor XII is activated during an incubation phase. Subsequently the reaction is started with calcium chloride. The time period until the sample clots is measured.

Reagents for carrying out this method have already been known for a long time and are distributed for example by the Baxter, Ortho and DiaMed Companies. Kaolin, silicate or ellagic acid are usually used as the activator.

The actual measurement is carried out by manual inversion of the analytical tubes and visual observation of thrombus formation. However, the clotting time can also be determined using optical or mechanical measurement instruments such as those that are marketed by the Amelung, Baxter, Labor and Behring Companies.

However, the conventional method described above has some significant drawbacks:

1. The activation phase must be assumed to be constant for all patients so that specific characteristics of the patients cannot be taken into account in the measurement. However, activation of the endogenous coagulation system and fibrinolysis that is also important for the haemorrhagic and thrombogenic tendency of the patient starts during this activation phase. Thus an incubation period that is too short leads to increased times, even in normal plasma, because activation is incomplete. The values also increase when the incubation periods are too long because the activated fibrinolytic system releases cleavage products from fibrinogen that retard coagulation.

2. A second disadvantage of the conventional method is that the analysis has to be carried out in two steps which increases the possibility of errors and makes it more difficult to standardize the determination methods.

3. Furthermore the fact that a current APTT determination is on the whole difficult to standardize is an important disadvantage of the existing method. The measurement results are usually determined in seconds, however, variations are inevitable in the production of the reagent since the activators are not exactly defined chemical substances that always have the same surface. In addition it is difficult to obtain the phospholipids necessary for the clotting process in a chemically pure form and to keep their activity constant. Variations in the measurement results from batch to batch are therefore inevitable. However, the variations in the results –if they are not too large –are accepted as being natural.

4. A fourth disadvantage is the poor automatability of the classical APTT determination. Other important coagulation tests such as thromboplastin time (PT) and fibrinogen are rapid reaction processes that can be carried out using a single test reagent, a two-step test with a relatively long preincubation period does not fit in well with the analytical processes when for example several parameters of the coagulation system are to be determined in parallel and substantially decreases the analytical throughput.

5. Furthermore it is desirable to start the reaction with plasma since this would considerably simplify the test procedure, calculation and analyzer functions.

The underlying technical problem of the present invention was therefore to avoid the disadvantages of the state of the art to as large an extent as possible i.e., in particular to enable an inclusion of the activation phase in the APTT reaction, a standardization of the results, a decrease in the number of pipetting steps and to allow the reaction to be started with the sample liquid, in particular plasma.

This problem was solved by a method for the determination of activated partial thromboplastin time (APTT) in a one-step reaction which is characterized in that the determination of APTT is started by contacting a reagent that contains the substances necessary for the APTT determination in a premixed form with a sample liquid.

In the method according to the invention the reagent can be placed in a vessel for the determination and then the reaction can be started by the addition of the sample liquid. On the other hand it is also possible to add the sample liquid first and start the reaction by addition of the premixed reagent. It is important that the determination is started by the direct contact of reagent and sample liquid without the activation phase necessary in the methods of the prior art being required.

The determination of APTT according to the method of the invention is preferably carried out by using blood or plasma that is diluted, if desired, particularly preferably by using plasma as the sample liquid.

The reagent for the determination of APTT contains the substances necessary for the determination of APTT in a premixed form. The necessary substances are usually an activator component, divalent cations and phospholipids. Kaolin, silicate or/and ellagic acid are preferably used as the activator. The concentrations of the activator are for example preferably 25 to 250 mg/l, particularly preferably 100 to 100 mg/l glass-wool-activated ellagic acid per liter reagent. The phospholipids contained in the reagent can be obtained from animal or/and vegetable tissue extracts or/and can be produced synthetically. Chloroform extracts from rabbit brain are an example of suitable phospholipids. The extract preferably from 0.2 to 1.0 g and particularly preferably from 0.4 to 0.6 g rabbit brain is used per liter reagent. The divalent cations present in the reagent are preferably calcium ions that are for example provided by adding calcium chloride to the reagent. The concentration of calcium ions in the analytical solution is preferably 5 to 15 mmol/l, particularly preferably 7.5 to 12.5 mmol/l.

In addition it is preferred that the reagent is stabilized by one or several amino acids. The shelf life of the reagent even at higher temperatures (e.g., 37° C.) is considerably increased by this stabilization. Amino acids that are selected from the group comprising D-alanine, L-alanine, β-alanine, glycine and valine are preferably used for the stabilization. Moreover it is preferred that the amino acids are present at a total concentration of 0.5 to 10% in relation to the total weight of the reagent.

It was surprisingly found that, contrary to all previous test instructions, it is possible to determine APTT in a one-step test procedure. Thus the activator and the phospholipids can be mixed with the divalent cations (e.g., calcium chloride) and this mixture can if desired be stabilized with amino acids (e.g., alanine). A premixed reagent is obtained in this way which contains all substances necessary to determine the APTT. It is now possible to start the reaction by directly contacting the sample liquid e.g., plasma with this reagent. Surprisingly the activation phase which was previously considered to be absolutely necessary can be omitted in the method according to the invention.

In a preferred embodiment of the method according to the invention the reagent is already packaged in vessels, in particular cuvettes. The reagent can be in a liquid or solid form e.g., as a solution or as a lyophilisate. The vessels are preferably made of an impervious transparent material such as e.g., polypropylene.

Moreover it is preferred that the vessels are sealed air and water-tight after dispensing the reagent. In order to achieve this a closure is for example used that consists of an aluminum foil seal. In this way it is possible to significantly simplify the determination of APTT and to integrate it into analytical systems for determining other parameters of the coagulation system by industrially packaging or pre-filling the vessels with the APTT reagents.

For this purpose it is additionally preferred that several vessels are integrated into one card i.e., in a common holder. Reagent- or/and batch-specific data can be stored on this holder or/and on the vessels themselves. Such a storage can for example be in the form of a bar code label.

In this manner batch-specific correction factors for the reagent can be used which significantly facilitate the standardization of results and thus their interpretation. Moreover the reagent components do not have to be pipetted in the laboratory which represents an optimization of the test and enables a great simplification of the computer program for controlling the analytical process and evaluating the results, in particular when the measuring vessels are industrially packaged or pre-filled e.g., when the measuring vessels are composed of an impervious material such as polypropylene and are hermetically sealed with a foil or cap.

The invention of the one-step test for determining APTT as described above also enables patient profiles to be prepared in a simple manner by for example additionally integrating the reagents for measuring thromboplastin time, fibrinogen, thrombin time and reptilase time into one reagent combination e.g., a card consisting of several vessels. It is also possible to adapt further coagulation tests such as coagulation factors (e.g., factors VIII, IX, X, XI, XII), protein S and protein C. In order to carry out the test it is only necessary to start the reaction with the patient's plasma. All test-specific information such as normal values, calibration curves etc. can be stored on a bar code and it is thus no longer necessary to provide a fresh normal plasma pool (FNP), a source of much error, and to establish calibration curves in the user's laboratory. When the analysis is carried out automatically, it is also not necessary to pipette reagents and the complicated logistic for this is superfluous. A combination of coded reagents with coded patient samples eliminates mistakes and thus leads to optimal, reliable results.

Thus a further object of the present invention is the combination of the method of determining APTT with further determination methods that can be carried out parallel to the APTT determination. Examples of this are further parameters of the coagulation system such as for example thromboplastin time (PT), fibrinogen concentration, thrombin time (TT), reptilase time (RT), coagulation factors, protein C and protein S.

The invention also concerns a reagent for the determination of the activated partial thromboplastin time (APTT) in a one-step reaction which contains all the substances necessary for the determination of APTT in a premixed form. Such a reagent usually contains phospholipids, an activator and divalent cations as specified above. The reagent is preferably stabilized by one or several amino acids as specified above. The reagent according to the invention differs from reagents of the prior art in that it contains all substances necessary for the APTT determination in a premixed form whereas in the case of the known reagents for the determination of APTT at least one essential component, usually the divalent ions, was lacking.

The reagent is preferably packaged or pre-filled in a vessel in a liquid or solid form (e.g., as a powder or lyophilisate) and can comprise several vessels integrated into one card and reagent- or/and batch-specific data can be stored on the vessels or/and on their holder.

A card with five measuring cuvettes for APTT tests can for example be used for this –as shown in FIG. 4 wherein data such as for example the expiry date of the reagents, lot number, value of the fresh normal plasma pool, conversion into other measurement units and correction factors can be stored on the card or/and on the measuring cuvettes themselves. As shown in FIG. 5 it is in addition possible to design such a card for a patient profile which can be used to carry out different analyses (e.g., APTT, PT, fibrinogen, TT and RT) in parallel.

Thus the present invention also provides a combination of reagents that comprises several vessels containing a reagent according to the invention for the determination of APTT and, if desired, further vessels for the determination of other parameters of the coagulation system.

Certain aspects of the invention are further elucidated on the basis of the figures:

BRIEF DESCRIPTION OF THE DRAWINGS

FIG. 1a shows the time course of coagulation for a method of determination of the prior art using normal plasma (the reaction is started conventionally with calcium chloride after a 3 minute preincubation), FIG. 1b shows the time course of coagulation for the determination method according to the invention (the reaction is started with normal plasma), FIG. 3 shows the correlation of both methods with different plasma samples.

The described invention is elucidated in more detail by the following examples.

EXAMPLE 1

Figure 2A:
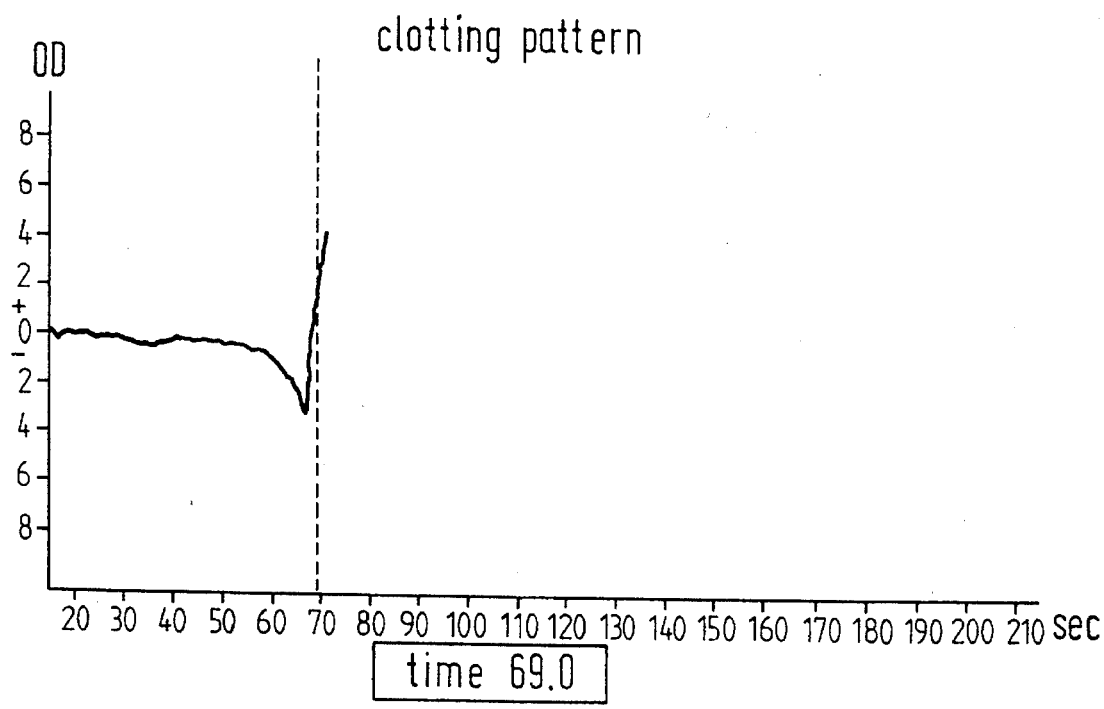
FIG. 2a shows the time course of coagulation for the determination method of the prior art using factor VIII-deficient plasma (the reaction is started with calcium chloride after a 3 minute preincubation)
Figure 2B:
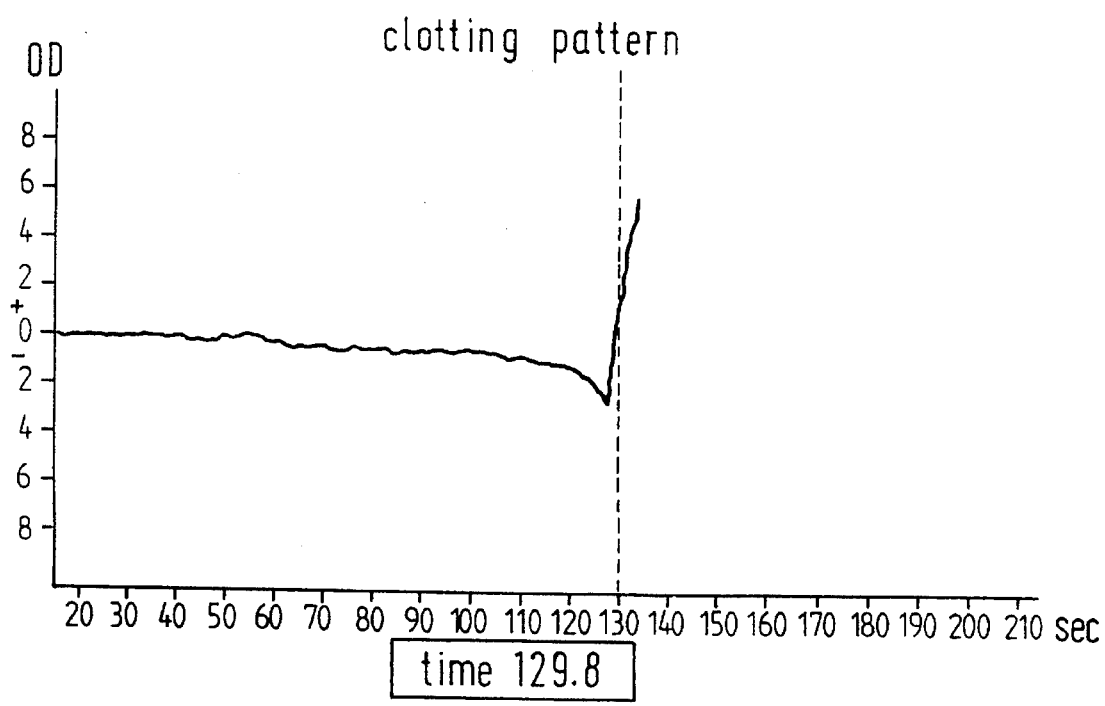
FIG. 2b shows the time course of coagulation for the determination method according to the invention (the reaction is started with factor VIII-deficient plasma)
Figure 4:
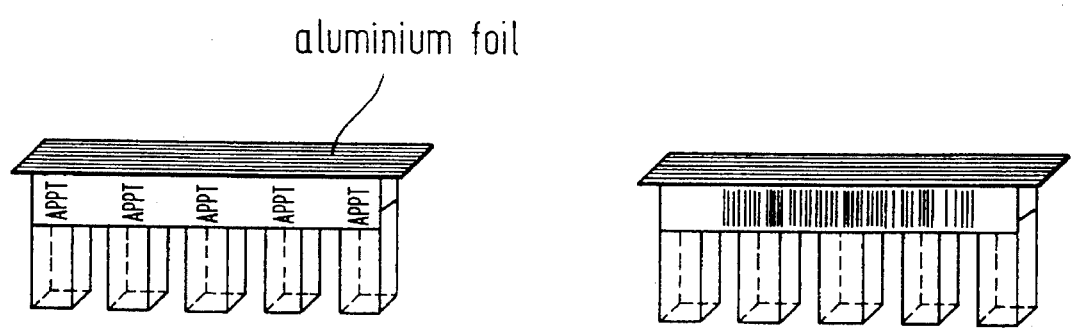
FIG. 4 shows the front and back of a card in which five measuring cuvettes are integrated. The expiry date of the reagents, lot number, value of the fresh normal plasma pool, conversion into other measuring units and correction factors can be recorded on the bar code on the back.

50 ml APTT reagent (DiaCelin, DiaMed) is mixed with ml 0.02 mol/l calcium chloride. 0.2 ml of this mixture is pipetted into cuvettes of the Labor Company. The reaction is started with 0.1 ml plasma. The coagulation time-course is monitored optically and recorded in an analyzer from the Labor Company (Coascreener). Normal plasma, abnormal plasma (average and high), heparin plasma (0.15 u/ml and 0.3 u/ml), factor-deficient plasma samples (factor VIII, IX, X, XI, XII, content ca. 1%) are used as the plasma samples. Parallel to this the plasma samples are analysed in a conventional manner according to the instructions using the reagents from the DiaMed Company. The results are summarized in Table 1, FIGS. 1 and 2 show two typical coagulation curves (normal plasma and factor VIII-deficient plasma); FIG. 3 shows the correlation between both methods and FIG. 4 shows a suitable card for several simultaneous determinations.

TABLE 1

| | Clotting time (sec) | |
|---|---|---|
| | Prior art method | Method according to the invention |
| normal plasma 1 (NP) | 27.5 | 85.4 |
| abnormal plasma 1 (AP1) | 59.3 | 141.3 |
| abnormal plasma 2 (AP2) | 97.7 | 184.2 |
| heparin plasma 1 (HP1) | 46.3 | 104.2 |
| heparin plasma 2 (HP2) | 80.5 | 132.5 |
| factor-deficient plasma VIII | 68.0 | 128.7 |
| factor-deficient plasma IX | 94.2 | 158.9 |
| factor-deficient plasma X | 103.5 | 145.0 |
| factor-deficient plasma XI | 86.1 | 145.4 |
| factor-deficient plasma XII | 150.9 | 151.9 |

EXAMPLE 2

The experiment according to example 1 is repeated with the addition of amounts of amino acids as stated in each case in order to improve the stability. The degree of stabilization at various concentrations is determined with normal plasma in a stress test by storing the reagent at 37° C. The results are summarized in Table 2. According to this the reagent is very well stabilized by D-alanine, L-alanine, β-alanine and glycine.

TABLE 2a

| | Clotting time in sec. | | | |
|---|---|---|---|---|
| D-alanine | start | 3 days 37° C. | 1 week 37° C. | 2 weeks 37° C. |
| 0% | 80 | 116 | 129 | 140 |
| 0.625% | 75 | 96 | 102 | 117 |
| 1.25% | 73 | 88 | 90 | 99 |
| 2.5% | 72 | 81 | 82 | 85 |
| 5.0% | 73 | 75 | 74 | 74 |

TABLE 2b

| | Clotting time in sec. | | | |
|---|---|---|---|---|
| L-alanine | start | 3 days 37° C. | 1 week 37° C. | 2 weeks 37° C. |
| 0% | 80 | 107 | 135 | 145 |
| 0.625% | 75 | 91 | 103 | 119 |
| 1.25% | 74 | 86 | 92 | 102 |
| 2.5% | 75 | 80 | 83 | 86 |
| 5.0% | 77 | 79 | 80 | 80 |

TABLE 2c

| | Clotting time in sec. | | | |
|---|---|---|---|---|
| β-alanine | start | 3 days 37° C. | 1 week 37° C. | 2 weeks 37° C. |
| 0% | 81 | 108 | 130 | 144 |
| 0.625% | 76 | 96 | 107 | 118 |
| 1.25% | 74 | 88 | 93 | 100 |
| 2.5% | 75 | 74 | 82 | 83 |
| 5.0% | 77 | 79 | 79 | 78 |

TABLE 2d

| | Clotting time in sec. | | | |
|---|---|---|---|---|
| glycine | start | 3 days 37° C. | 1 week 37° C. | 2 weeks 37° C. |
| 0% | 81 | 110 | 136 | 136 |
| 0.625% | 76 | 92 | 98 | 103 |
| 1.25% | 75 | 84 | 90 | 92 |
| 2.5% | 75 | 79 | 82 | 80 |
| 5.0% | 83 | 85 | 87 | 87 |

TABLE 2e

| | Clotting time in sec. | | | |
|---|---|---|---|---|
| valine | start | 3 days 37° C. | 1 week 37° C. | 2 weeks 37° C. |
| 0% | 86 | 111 | 130 | 145 |
| 0.625% | 80 | 98 | 106 | 126 |
| 1.25% | 79 | 91 | 95 | 105 |
| 2.5% | 78 | 88 | 92 | 96 |
| 5.0% | 82 | 91 | 94 | 95 |

TABLE 2f

| | Clotting time in sec. | | | |
|---|---|---|---|---|
| lysine | start | 3 days 37° C. | 1 week 37° C. | 2 weeks 37° C. |
| 0% | 78 | 108 | 131 | 140 |
| 0.625% | 80 | 91 | 104 | 128 |
| 1.25% | 93 | 106 | 120 | 118 |
| 2.5% | 160 | 202 | — | — |
| 5.0% | >250 | — | — | — |

TABLE 2g

| methionine | Clotting time in sec. | | | |
|---|---|---|---|---|
| | start | 3 days 37° C. | 1 week 37° C. | 2 weeks 37° C. |
| 0% | 81 | 108 | 125 | 140 |
| 0.625% | 75 | 94 | 99 | 119 |
| 1.25% | 76 | 90 | 95 | 110 |
| 2.5% | 81 | 95 | 96 | 110 |
| 5.0% | 105 | 122 | — | — |

TABLE 2h

| glutamic acid | Clotting time in sec. | | | |
|---|---|---|---|---|
| | start | 3 days 37° C. | 1 week 37° C. | 2 weeks 37° C. |
| 0% | 82 | 110 | 131 | 142 |
| 0.625% | 74 | 93 | 102 | 120 |
| 1.25% | 72 | 86 | 91 | 102 |
| 2.5% | 78 | 87 | 92 | 103 |
| 5.0% | 122 | 160 | 168 | 180 |

TABLE 2i

| N-acetyl-cysteine | Clotting time in sec. | | | |
|---|---|---|---|---|
| | start | 3 days 37° C. | 1 week 37° C. | 2 weeks 37° C. |
| 0% | 83 | 117 | 137 | 142 |
| 0.625% | 122 | 166 | 176 | >250 |
| 1.25% | 228 | >250 | — | — |
| 2.5% | >250 | — | — | — |
| 5.0% | >250 | — | — | — |

TABLE 2j

| aspartic acid | Clotting time in sec. | | | |
|---|---|---|---|---|
| | start | 3 days 37° C. | 1 week 37° C. | 2 weeks 37° C. |
| 0% | 81 | 109 | 135 | 136 |
| 0.625% | 74 | 88 | 102 | 109 |
| 1.25% | 73 | 83 | 90 | 92 |
| 2.5% | 77 | 82 | 89 | 88 |
| 5.0% | 110 | 118 | 140 | 130 |

TABLE 2k

| arginine | Clotting time in sec. | | | |
|---|---|---|---|---|
| | start | 3 days 37° C. | 1 week 37° C. | 2 weeks 37° C. |
| 0% | 83 | 117 | 132 | 140 |
| 0.625% | 83 | 85 | 125 | 141 |
| 1.25% | 103 | 165 | 160 | 165 |
| 2.5% | 214 | >250 | — | — |
| 5.0% | >250 | — | — | — |

EXAMPLE 3

The experiment according to example 1 is repeated, however, the thromboplastin time (PT), fibrinogen (Fib), thrombin time (TT) and reptilase time (RT) are also determined simultaneously. Reagents from the DiaMed Company are used. The reagents are used as follows:

a) DiaPlastin for measuring the thromboplastin time (PT)

0.2 ml of the reagent is pipetted into the first cuvette. The reaction is started with 0.1 ml plasma.

b) DiaCelin for measuring the activated partial thromboplastin time (APTT)

0.2 ml of the reagent –prepared as in example 1–is pipetted into the second cuvette. The reaction is started with 0.1 ml plasma.

c) Fibrinogen reagent for the determination of the fibrinogen concentration

The thrombin reagent is mixed 1+1 with Owren buffer, 0.2 ml thereof is pipetted into the third cuvette. The reaction is started with 0.02 ml plasma.

d) DiaThrombin for the determination of the thrombin time (TT).

The lyophilisate is dissolved in 31 ml distilled water. 0.2 ml thereof is pipetted into the fourth cuvette. The reaction is started with 0.2 ml plasma.

e) DiaReptin for the determination of the reptilase time (RT)

0.1 ml of the reagent is diluted with 3 ml distilled water. 0.2 ml of the dilution is piperred into the fifth cuvette. The reaction is started with 0.2 ml plasma.

Figure 5:
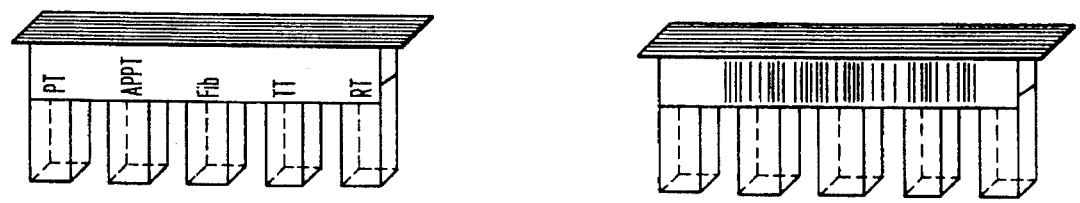
FIG. 5 shows front and back of a card in which for example five measuring cuvettes are likewise integrated. In this case the card is designed for a patient profile and can be used to carry out various analyses simultaneously. The bar code on the back contains all data as in FIG. 4.

The results of example 3 are summarized in Table 3 and show that the methods compare well. FIG. 5 shows a card with which these determinations can be carried out simultaneously with a patient's plasma.

TABLE 3

| | Clotting time (sec) | | | | | | | | | |
|---|---|---|---|---|---|---|---|---|---|---|
| | PT | | APTT | | Fib | | TT | | RT | |
| | old | new | old | new | old | new | old | new | old | new |
| Normal plasma 1 | 12.0 | 11.7 | 28.3 | 89.0 | 11.5 | 11.5 | 18.5 | 19.5 | 20.8 | 20.1 |
| Abnormal plasma 1 | 18.9 | 18.4 | 61.0 | 148.0 | 21.2 | 20.3 | 15.2 | 15.5 | 26.9 | 27.1 |
| Abnormal plasma 2 | 27.5 | 26.5 | 97.0 | 188.0 | 22.0 | 20.7 | 15.9 | 15.9 | 33.3 | 32.7 |
| Heparin plasma 1 | 13.0 | 13.4 | 43.0 | 110.0 | 13.4 | 13.1 | >250 | >250 | 21.3 | 20.7 |
| Heparin plasma 2 | 13.9 | 13.7 | 82.0 | 137.0 | 13.5 | 12.6 | >250 | >250 | 19.8 | 21.3 |

EXAMPLE 4

The experiment according to example 3 is repeated. However, the reagents are previously dispensed into cuvettes made of polypropylene and are sealed tight with an aluminum foil. The results are summarized in Table 4. It turns out that pre-dispensing and sealing the reagents does not alter the results.

TABLE 4

| | Clotting time (sec) | | | | | | | | | |
|---|---|---|---|---|---|---|---|---|---|---|
| | PT | | APTT | | Fib | | TT | | RT | |
| | sealed | normal | sealed | normal | sealed | normal | sealed | normal | sealed | normal |
| Normal plasma 1 | 11.8 | 11.8 | 86.8 | 88.4 | 10.8 | 10.8 | 21.0 | 21.0 | 19.8 | 19.9 |
| Abnormal plasma 1 | 18.5 | 17.9 | 145.0 | 147.0 | 19.3 | 19.0 | 17.3 | 17.1 | 26.4 | 26.3 |
| Abnormal plasma 2 | 26.2 | 26.7 | 188.0 | 188.0 | 17.8 | 18.1 | 17.1 | 17.4 | 30.6 | 32.3 |
| Heparin plasma 1 | 13.5 | 13.1 | 108.0 | 109.0 | 11.4 | 11.8 | >250 | >250 | 19.9 | 21.1 |
| Heparin plasma 2 | 13.3 | 13.2 | 137.0 | 138.0 | 12.9 | 12.2 | >250 | >250 | 20.7 | 20.0 |

I claim:

1. A method for the determination of the activated partial thromboplastin time (APTT) in a one-step reaction comprising.
   a) providing a reagent that contains an activator, phospholipids and divalent cations in a premixed form,
   b) contacting a sample liquid with the reagent of step a), and
   c) measuring the time course of coagulation.

2. The method of claim 1, wherein plasma is used as the sample liquid.

3. The method of claim 1, wherein the activator is selected from the group consisting of kaolin, silicate, ellagic acid, and mixtures thereof.

4. The method of claim 1, wherein the phospholipids are selected from the group consisting of phospholipids obtained from animal tissue, phospholipids obtained from vegetable tissue, phospholipids produced synthetically, and mixtures of the above.

5. The method of claim 1, wherein the divalent cations are calcium ions.

6. The method of claim 1, wherein the reagent comprises at least one amino acid.

7. The method of claim 6, wherein the amino acid is selected from the group consisting of D-alanine, L-alanine, β-alanine, glycine and valine.

8. The method of claim 6, wherein the amino acids are present at a total concentration of 0.5 to 10% in relation to the total weight of the reagent.

9. The method of claim 1, wherein the reagent is packaged or pre-dispensed in a vessel.

10. The method of claim 9, wherein the vessel is sealed and is air- and water-tight.

11. The method of claim 9, wherein the vessel is sealed with a seal of aluminum foil.

12. The method of claim 9, wherein multiple measuring vessels are integrated into one card.

13. The method of claim 9, wherein the vessel, card, or material accompanying the vessel or card contains reagent-specific or batch-specific data.

14. The method of claim 9, wherein the reagent-specific or batch-specific data is on a bar code label.

15. The method of claim 1, wherein measurement of the coagulation time is carried out in a mechanical or optical analytical system.

16. The method of claim 1, wherein the method is carried out contemporaneously with other measurements, wherein the other measurements include at least one measurement of the coagulation system selected from the group consisting of thromboplastin time, fibrinogen concentration, thrombin time, reptilase time, coagulation factors, protein C and protein S.

17. A reagent for the determination of the activated partial thromboplastin time in a one-step reaction comprising an activator, phospholipids and divalent cations in a premixed form.

18. The reagent of claim 17, further comprising at least one amino acid.

19. The reagent of claim 18, wherein the amino acid is selected from the group consisting of D-alanine, L-alanine, β-alanine, glycine and valine.

20. The reagent of claim 18, wherein the amino acids are present at a total concentration of 0.5 to 10% in relation to the total weight of the reagent.

21. The reagent of claim 17, wherein the reagent is packaged or predispensed in a vessel.

* * * * *

UNITED STATES PATENT AND TRADEMARK OFFICE
CERTIFICATE OF CORRECTION

PATENT NO. : 5,506,146
DATED : April 9, 1996
INVENTOR(S) : JOSEF

It is certified that error appears in the above-indentified patent and that said Letters Patent is hereby corrected as shown below:

On the title page,
Item [73], please delete "Praz-Rond, Germany and insert therefor -- Cressier sur Morat, Switzerland --.

Signed and Sealed this

Third Day of December, 1996

Attest:

BRUCE LEHMAN

*Attesting Officer*  *Commissioner of Patents and Trademarks*